United States Patent [19]

Kaiser et al.

[11] 4,373,518
[45] Feb. 15, 1983

[54] METHOD OF DRILLING LIVING BONE

[75] Inventors: William L. Kaiser, Warsaw; Gale R. Brown, South Whitley, both of Ind.

[73] Assignee: Zimmer, Inc., Warsaw, Ind.

[21] Appl. No.: 191,187

[22] Filed: Sep. 26, 1980

[51] Int. Cl.³ .............................................. A61F 5/04
[52] U.S. Cl. ............................ 128/92 EB; 128/92 B; 128/310
[58] Field of Search ............... 128/92 R, 92 B, 92 A, 128/92 BA, 92 BB, 92 EB, 305.1, 310; 408/227, 228, 229, 230

[56] References Cited

U.S. PATENT DOCUMENTS

| | | | |
|---|---|---|---|
| 385,088 | 6/1888 | Benzie | 408/227 |
| 777,543 | 12/1904 | Rich | 408/227 |
| 2,981,127 | 4/1961 | Ransom | 408/229 |
| 3,199,381 | 8/1965 | Mackey | 408/230 |
| 3,727,611 | 4/1973 | Schultz | 128/92 EB |
| 3,809,074 | 5/1974 | DeMoude | 128/92 A |
| 3,892,232 | 9/1975 | Neufeld | 128/92 EB |
| 4,231,692 | 11/1980 | Brabetz et al. | 408/230 |
| 4,231,693 | 11/1980 | Kammeraad | 408/230 |
| 4,257,307 | 3/1981 | Regensburger | 408/228 |
| 4,265,231 | 5/1981 | Scheller, Jr. et al. | 128/92 EB |
| 4,299,212 | 11/1981 | Goudfrooy | 128/92 EB |
| 4,312,337 | 1/1982 | Donohue | 128/92 EB |

FOREIGN PATENT DOCUMENTS 2043458 10/1980 United Kingdom .

OTHER PUBLICATIONS

Machinery's Handbook, by Oberg, Jones & Horton, 20th Ed., 5th Printing 1978, pp. 1806-1807.
Stanley Tools Full Line Catalog 1979/1980, p. 10.
"Temperatures Measured In Human Cortical Bone When Drilling," Matthews et al., *The Journal of Bone and Joint Surgery*, Mar. 1972, vol. 54-A, No. 2, pp. 297-308.

Primary Examiner—Kyle L. Howell
Assistant Examiner—C. W. Shedd
Attorney, Agent, or Firm—Margaret L. Geringer

[57] ABSTRACT

This invention relates to a method of using a half-drill for drilling holes in living bone for orthopaedic operations. The invention also relates to a method of using a half-drill tip on skeletal bone pin for drilling holes in living bone and subsequently using that skeletal pin with external immobilization devices or alone in circumstances where a Steinmann Pin or large Kirschner wire might commonly be selected.

1 Claim, 11 Drawing Figures

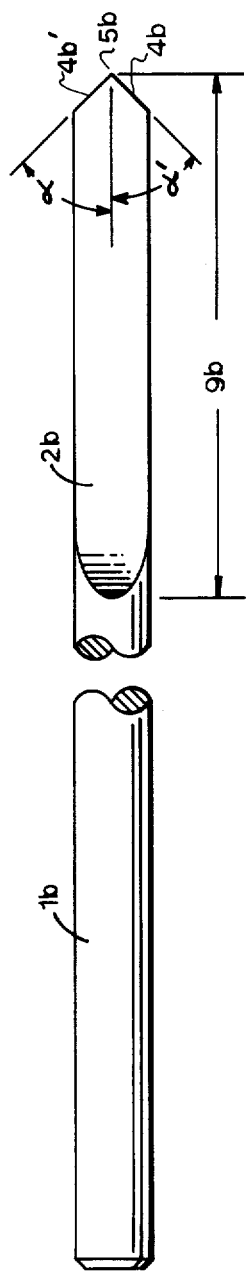
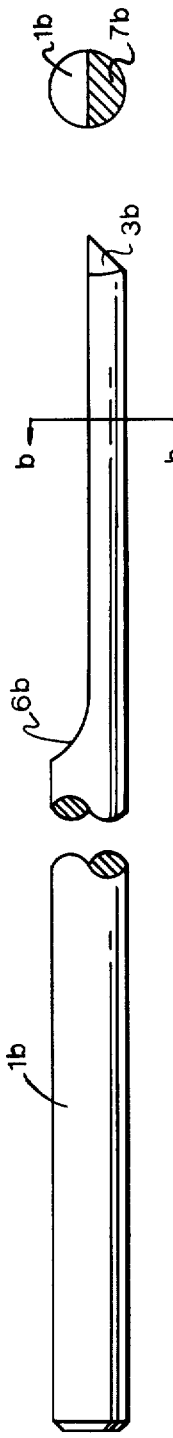
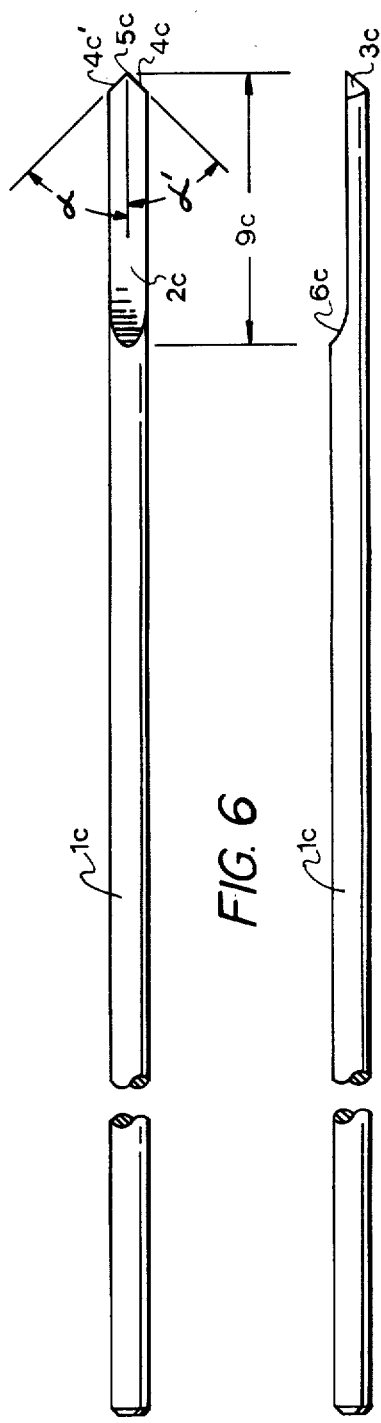
FIG. 4   FIG. 5a   FIG. 5b   FIG. 6   FIG. 7

METHOD OF DRILLING LIVING BONE

BACKGROUND OF THE INVENTION

The design of a half-drill has been used in the aircraft sheet metal and arms manufacturing industries, among other industrial applications for many years. The half-drill was often used to hold a tight tolerance of a drill hole for precision industrial drilling. The concept of a half-drill tip design is not known to have ever been used before for use in living bone.

A half-drill, such as that used in the sheet metal industry, is shown in FIG. 1 and is comprised of an elongated cylindrical shaft 1a having a cutting tip 9a at the distal end of the shaft 1a. The cutting tip 9a has a semi-circular cross-section. One-half side of the cylindrical shaft is milled away at the distal end of the shaft to produce the semi-cylindrical tip. This provides a longitudinally flat surface 2a along a center plane of the drill. The cutting tip 9a is further prepared by providing a taper 3a which produces two angled edges 4a' and 4a at the distal end of the flat surface 2a, and which produces a radial relief on the non-cutting edge. The two edges 4a' and 4a come together at a center point 5a.

FIG. 2 illustrates another embodiment of a prior art half-drill which utilizes a pilot tip 8a at the distal end of the cutting tip 9a'. The pilot tip 8a has a smaller diameter than the proximal end of the cutting tip 9a'. The proximal end of the tip 9a' has a diameter equal to the diameter of the shaft 1a.

Drills are used in orthopaedic surgery to drill holes in bone to prepare a channel for bone screws which are used for the fixation of bone or with bone screws used in conjunction with bone plates for the fixation and stabilization of bone. Typically, a standard twist drill is used for this type of routine drilling.

There are a number of disadvantages to using standard twist drills for direct drilling of bone. A standard helical, twist drill must be started perpendicular to the bone's surface to prevent its slipping out of position. Also, when a twist drill is just ready to proceed through the wall of cortical bone, the drill "grabs", takes a large forward motion and requires a great increase in torque to continue rotation. This irregular rough action can fracture the bone or can cause excessive unanticipated and uncontrolled penetration into soft tissue. This is a danger particularly to nerves and blood vessels.

Helical or twist drills of different sizes, cutting angles, rake angles and material compositions have been used in orthopaedic surgery for many decades.

A variety of bone pins are also commonly used in orthopaedic surgery with external skeletal immobilization devices or alone. In cases where bone pins are used with external fixation devices, the bone pins are drilled directly through the flesh and into the bone, and then left in place to be attached to an external immobilization device. One reason why twist drill tips are not used on these bone pins is because problems would be encountered with the potential for damaging nerves and blood vessels which could potentially become trapped and wound-up by a helical twist drill.

Fixation pins and wires standardly used today often have three or four facet trochar tips or spade style tips. A three facet trocar tip 15 and a spade style tip 14 are shown as examples of prior art in FIG. 3. Another style tip 16 shown in FIG. 3 will be referred to as an arrowhead tip. The biggest disadvantage of these pins, as well as other known styles of bone pins, is the excessive amount of heat generated, which can cause thermal necrosis or death of tissue due to heat. Larry S. Matthews, M.D. and Carl Hirsh, M.D., Ph.d. have written an article entitled "Temperatures Measured in Human Cortical Bone When Drilling," copyrighted 1972 by *The Journal of Bone and Joint Surgery*, Vol. 54-A, No. 2, pp. 297-308, March, 1972. This article notes other references indicating that thermal necrosis due to drilling has been reported, and that the relationship of thermal necrosis to a loss of stability in fixation is established. The article goes on to discuss that thermal damage to living tissue is related to the magnitude of temperature elevation and the period of time during which the tissue is subjected to damaging temperatures. Heat generated when drilling is due to friction and to the fragmentation of particles of bone at the cutting edge of the drill. It is to be noted that bone pins having a tip such as the spade, arrowhead or trochar tip do not allow for the extrusion of bone chips as the drilling progresses. Therefore, with these types of tips the bone chips are compressed into the hole wall causing further mechanical damage. Although a twist drill style tip allows for chip removal, as previously stated, the twist drill tip is not suitable for many types of bone drilling for external fixation. Twist drills also do not present the thermal problem that the current bone pins present, yet twist drills are not suitable for drilling through living flesh. It is also noted that much greater temperature elevations are noted when a worn drill is used.

OBJECTS OF THE INVENTION

The principle object of the invention is to provide a method of forming holes in living bone to prepare a channel for orthopaedic fixation devices which allows the drill to be applied to the bone surface at angles other than perpendicular to the bone surface without slipping out of position as the drilling proceeds at this angle.

A further object of the invention is to provide a method of drilling holes in bone to prepare a channel for orthopaedic fixation devices which allows the drill to proceed smoothly through the wall of cortical bone without grabbing and lunging forward, and without requiring a great increase in torque to continue rotation.

A still further object of the invention is to provide a method of drilling with a bone pin in living bone and other tissue for orthopaedic operations which allows for extrusion of cutting chips (bone chips), from the hole and which does not cause the extent of thermal necrosis that other bone pins do.

A still further object of this invention is to provide an improved half-drill tip for use on drills and bone pins.

SUMMARY OF THE INVENTION

The present invention accomplishes all of the above objects of invention. The method of drilling described in this invention employs the half-drill style cutting tip. The term drilling is meant to include standard drilling procedures as well as reaming procedures. Half-drills have never before been known to be used for drilling of any sort in living tissue, including bone. The use of a half-drill for orthopaedic use offers beneficial and unexpected results. The use of half-drills as bone drills to replace the conventional twist drill operations allows the drill to be used on angles up to 40 degrees from the perpendicular without slipping. It also allows the drill to proceed smoothly out of the cortical bone.

The use of half-drill tips on bone pins allows for extrusion of bone chips and hence less friction when drilling. The maximum drilling temperatures are significantly less than those achieved with conventional bone pins. Also, the period of time during which the tissue is subjected to damaging temperatures is also significantly less with the half-drill pins than with the conventional bone pins. This combination offers a benefit of less thermal damage to bone and hence better stabilization.

BRIEF DESCRIPTION OF THE DRAWINGS

In order that the principles of the present invention may be readily understood, various examples of the prior art, as well as various embodiments of the present invention will be described with reference to the accompanying drawings, which form part of the original disclosure of this application, and wherein:

FIG. 4 is a top longitudinal view of an embodiment of the half-drill used in the method of drilling bone described by this invention.

FIG. 5a illustrates a side longitudinal view of the half-drill of FIG. 4.

FIG. 5b illustrates a sectional view of the cutting tip taken along lines b—b of FIG. 5a.

FIG. 6 illustrates a top longitudinal view of an embodiment of a bone fixation pin utilizing a half-drill cutting tip as described in the method of drilling bone described by this invention.

FIG. 7 is a side longitudinal view of the bone fixation pin of FIG. 6.

FIG. 8b is a fragmentary auxiliary view of the modified half-drill cutting tip of FIG. 8a.

FIG. 9 is a fragmentary side longitudinal view of the modified half-drill cutting tip of FIG. 8a.

DETAILED DESCRIPTION OF THE INVENTION

Figure 1:
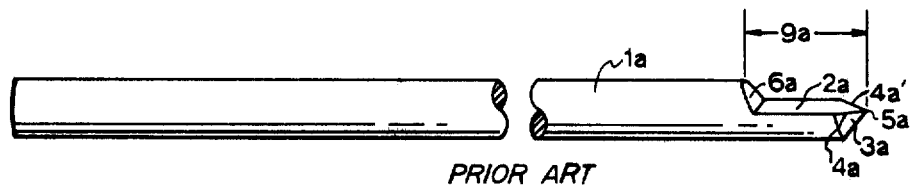
FIG. 1 illustrates a pictorial view of a prior art half-drill.
Figure 2:
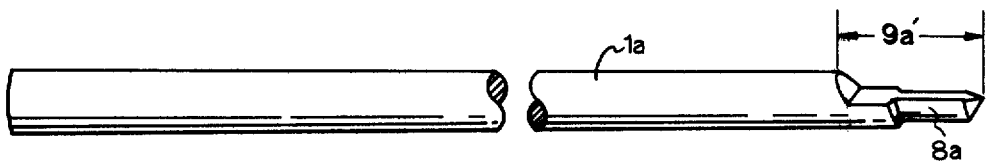
FIG. 2 illustrates a pictorial view of another embodiment of the prior art half-drill.

The invention described here is a method of drilling bone comprised of cortical and cancellous bone, utilizing a half-drill cutting tip. Half-drills are not known to have ever been used in orthopaedics. Unexpected cutting benefits result from the use of the half-drill style cutting tip. The tip can be utilized in conjunction with at least two general categories of drilling: (1) operations usually requiring a standard twist drill bit, and (2) operations in which some type of bone pin is used for a drilling operation. The benefits of both of these general categories vary due to the different circumstances under which one would be using a drill bit or a bone pin.

Routine drilling procedures are usually used in circumstances where holes are being drilled directly into the bone for the purpose of drilling holes in bone either for preparing a hole for bone screws or for other internal fixation devices. As previously stated, helical twist drills are generally used for these procedures. The use of a half-drill such as that shown in FIGS. 4 and 5 overcomes many problems which are associated with the helical twist drills. The use of a half-drill allows the cutting tip 9b of the half-drill to be applied to the bone surface at an angle up to 40 degrees away from the perpendicular. The drill is able to enter the cortical bone in this angle range without slipping away from its initial location. This is a contrast to twist drills which must be started perpendicular to the bone's surface to prevent its slipping or "walking" out of position.

Position and alignment of holes are extremely important in orthopaedic surgery for proper and optimum placement of any fixation device. The added 80 degree range (40 degrees on either side of the perpendicular) gives the surgeon much more flexibility in operations, especially when the site for the drill hole is not easily accessible or it is difficult to approach the bone with the drill perpendicular. Oftentimes it is more desirable, due to the specific operation, to approach the bone at an angle other than 90 degrees. Therefore, this greater angle range greatly facilitates hole, and therefore screw, placement particularly in hip nailing, bone plating and other fracture reconstruction.

The use of a half-drill also solves another problem typically encountered with twist drills. When the drill is just ready to proceed out of the wall of cortical bone, a helical or twist drill "grabs", takes a large forward motion and requires a great increase in torque to continue rotation. This irregular rough action can fracture the bone or can cause excessive unanticipated and uncontrollable penetration into soft tissue, a danger particularly to nerves and blood vessels. With use of a half-drill, this problem is avoided, and the drill proceeds smoothly out of the wall of cortical bone without grabbing or lunging forward.

Like the half-drill described in the prior art which has been used in the aircraft, sheet metal and arms manufacturing industries, the half-drill used in the method of drilling bone described above, is as shown in FIGS. 4 and 5a and 5b. The drill has an elongated cylindrical shaft 1b with a cutting tip 9b at one end of the shaft. The cutting tip 9b is comprised of a semi-cylindrical portion illustrated by cross-section 7b of FIG. 5b. The semi-cylindrical portion has a flatplane 2b along a center plane of the drill. The tip 9b has a proximal end and a distal end wherein the proximal end is integrally connected to the shaft 1b by a sloped surface 6b. The cutting tip 9b is further prepared by providing a taper 3b, which produces two angled edges 4b' and 4b at the distal end of the flat surface 2b, and which produces a radial relief on the non-cutting edge 4b. The two edges 4b' and 4b come together at a center point 5b. The angled edge 4b' is the cutting edge. The preferred angle $\alpha$ of the taper is approximately 45 degrees from the center axis of the cylindrical shaft 1b and $\alpha'$ is approximately 42 degrees from the center axis of the cylindrical shaft 1b. The length of the cutting tip 9b is approximately two to three centimeters in length in the preferred embodiment.

Half-drills also allow for the removal of bone chips which result from the drilling. Therefore, as previously stated in the Background Information, not as much heat is built up with a half-drill style cutting tip. Since twist drills also allow for chip removal, the temperature aspect is not as much of a problem with twist drills as there is with the type of tips currently used on bone pins.

It is not practical to use a twist style tip on bone pins, such as Steinman Pins or Kirschner Wire for many reasons. First of all, it is much too expensive to put a helical twist tip on bone pins and wires that are probably only going to be used once. It would also be difficult to put a helical twist tip on bone pins which are often quite thin in comparison to drill bits. Also, as previously stated, since bone pins are often drilled right through the flesh and into the bone, potential exists for damage to nerves and blood vessels and fleshy tissue which may get trapped or wound up by a helical twist drill. When bone pins are used for external fixation, the pin would in fact pass through the patient's bone and then be left in that position within the bone for a period of time. Therefore, it is necessary to preserve the strength and viability of the bone immediately surrounding the pin when using external immobilization devices.

Figure 3:
FIG. 3 illustrates three types of tips used on prior art bone fixation pins, and includes a longitudinal view and corresponding end view for each type of pin, with the three end views being enlarged relative to the longitudinal views.
Figure 3:
Figure 3:
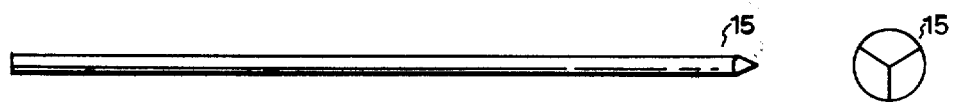
Figure 3:
Figure 3:
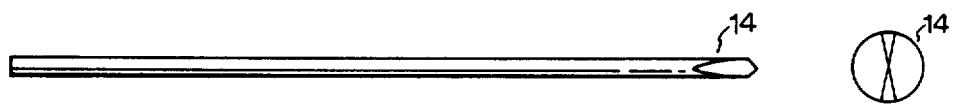
Figure 3:
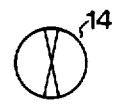

Therefore, tips such as those shown in FIG. 3 are typically used on bone pins such as Steinman Pins and Kirschner Wire. The trochar point 15, spade point 14, and arrowhead point 16 are simple in design, but do not allow for bone chip removal. Since the heat generated by drilling is due to friction, and to the fragmentation of particles of bone at the cutting edge of the drill, tip styles such as those shown in FIG. 3 only add to the heat problem as well as cause additional mechanical damage to the bone.

The utilization of the half-drill cutting tip on bone pins as shown in FIGS. 6 and 7 allows for the removal of bone chips. Structurally, the tip is identical to that described in FIGS. 4 and 5 except the corresponding numbers have a "c" after the number instead of a "b". The bone pins are typically longer than the drill bits.

The most beneficial advantage to using the half-drill tip on bone pins is the substantial reduction in maximum temperature elevation and the substantial reduction in the period of time during which tissue, such as bone, is subjected to damaging temperatures. The use of the half-drill bone pins generates far less heat upon insertion than any other known similar pins. Therefore, far less thermal damage to bone is to be expected resulting in stronger stability in bone fixation.

For the purposes of this invention, the time period during which bone is subjected to damaging temperatures will be measured for the length of time the bone temperature is greater than 55 degrees centigrade. Since thermal damage is a combination of the length of exposure to damaging temperatures in combination with the maximum elevation of temperature reached, the choice of 55 degrees centigrade is somewhat arbitrary and yet provides a relative standard. In one example cited in the Matthews/Hirsch article previously cited, it was reported that some experimenters found necrosis of osteocytes in long bones of rabbits when they were exposed to a temperature elevation of 55 degrees centigrade for one minute. Other experimenting indicates that the temperature range around 55 degrees centigrade is damaging to bone and can cause thermal necrosis.

Experimental results of average maximum temperatures measured in cortical bone using the standard half-drill bone pin of the type shown in FIGS. 6 and 7 and the trocar point, spade and arrowhead points of FIG. 3 are tabulated in Table 1. Experimental results of the average duration of temperature elevation above 55 degrees centigrade for the same styles of pins are shown in Table 2.

TABLE 1

AVERAGE MAXIMUM TEMPERATURES OF CORTICAL BONE

| Radial Distance From The Drill Site (mm) | Standard half-drill bone pin | Modified half-drill bone pin | Trocar point bone pin | Spade point bone pin | Arrowhead point bone pin |
|---|---|---|---|---|---|
| 0.5 | 67.85° C. | 68.25° C. | 116.3° C. | 111.5° C. | 100.6° C. |
| 1.0 | 51.6° C. | 51.15° C. | 96.2° C. | 93.7° C. | 75.0° C. |
| 2.0 | 31.1° C. | 31.80° C. | 60.5° C. | 62.1° C. | 47.0° C. |
| 3.0 | 27.05° C. | 29.98° C. | 50.6° C. | 47.7° C. | 41.1° C. |

TABLE 2

AVERAGE DURATION OF TEMPERATURE ELEVATION ABOVE 55 DEGREES CENTIGRADE

| Radial Distance from the Drill Site (mm) | Standard half-drill bone pin | Modified half-drill bone pin | Trocar Point bone pin | Spade point bone pin | Arrowhead point bone pin |
|---|---|---|---|---|---|
| 0.5 | 2.71 sec. | 1.97 sec. | 41.28 sec. | 42.30 sec. | 26.46 sec. |
| 1.0 | 1.06 sec. | 1.01 sec. | 37.86 sec. | 40.50 sec. | 17.52 sec. |
| 2.0 | 0 sec. | 0 sec. | 9.66 sec. | 26.94 sec. | 1.14 sec. |
| 3.0 | 0 sec. | 0 sec. | 2.94 sec. | 12.90 sec. | 0 sec. |

Note that measurements are taken in each case at varying distances measured radially outward from the drill site in the bone. At 0.5 millimeters from the drill site of the standard half-drill bone pin of FIGS. 6 and 7, the average maximum temperature using a half-drill is only 67.85 degrees centigrade and the length of time the temperature is greater than 55 degrees centigrade is only 2.71 seconds. This is contrasted to the trocar point at the same distance which had an average maximum temperature of 116.3 degrees centigrade and an average duration of 41.28 seconds that the temperature was greater than 55 degrees centigrade. With the diamond tip, the average maximum temperature at 0.5 millimeters from the pin site was 111.5 degrees centigrade, with an average duration of 42.30 seconds that the temperature was greater than 55 degrees centigrade. With the arrowhead point, the average maximum temperature at 0.5 millimeters from the pin site was 100.6 degrees centigrade, with an average duration of 26.46 seconds that the temperature was greater than 55 degrees centigrade.

At 1.0 millimeter from the pin site for the standard half-drills, the average maximum temperature is 51.6 degrees centigrade. The average here was less than 55 degrees centigrade, and the average duration that the temperature was greater than 55 degrees centigrade was only 1.06 seconds. The comparable temperatures and times for the other tips can be better compared by looking at the tables. In general, the half-drill of this invention produced significantly lower maximum temperatures and remained above 55 degrees centigrade for a significantly less period of time than other known bone pins at each distance from the drill site.

All test results shown were done by hand drilling. As can be seen by the test results, use of a half-drill style bone pin produces measurably lower temperatures than other known similar pins. The lower drilling temperatures of the half-drill bone pins offer a significant benefit to surgeons by decreasing the danger of thermal necrosis.

Half-drill bone pins can be used in all applications where standard Steinmann Pins or large Kirschner Wire would otherwise be used. They would probably be most frequently used for stabilization of fracture fragments in association with a strong external framework. They can be used as half-pins which use only one external support.

The half-drill cutting tip could also prove advantageous for reaming of medullary canals for intramedullary fracture fixation or total joint revision.

The use of the half-drill cutting tip on the bone pins also offers the angle range advantage and the advantage of not grabbing as it proceeds out of the cortical bone as discussed in conjunction with the drill bit use. Although other styles of bone pins tend to have these features also, they don't offer the temperature benefits that the half-drill does.

The half-drill bone pin is considered easier to introduce to the bone, control and direct than standard bone pins having spade trochar or arrowhead style points.

The half-drill tip described is simple in construction and therefore inexpensive to produce. This lower cost should be beneficial in itself, especially compared to twist drills. This lower cost will lead to earlier replacement of drills before excessive drilling has occurred. Dull cutting edges also tend to cause increased drilling temperatures, so this would be a good advantage.

The drill bits and bone pins can be made of any material suitable for use in the body. 316 L stainless steel could provide for a less expensive style which could be used as a disposable drill if desired. MP-35N which is a very hard, tough metal could be used for the drill which should hold a good cutting edge for many operations.

Figure 8A:
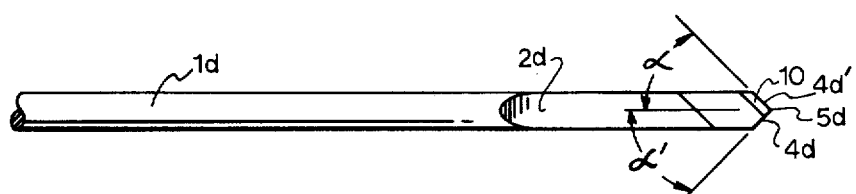
FIG. 8a is a fragmentary top longitudinal view of a modified half-drill cutting tip for use on bone pins and drills.
Figure 8B:
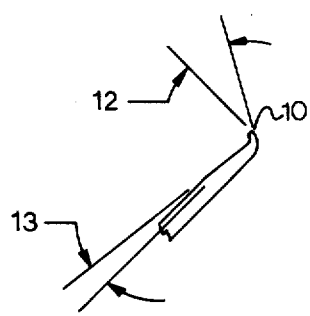
Figure 9:
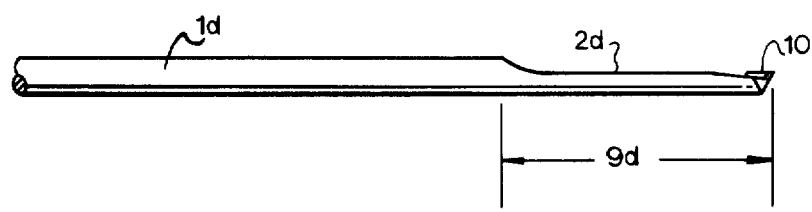

A further embodiment of the invention includes a modification to the design of the half-drill cutting tip. This modified cutting tip 9d is illustrated in FIGS. 8a, 8b and 9. The modified design can be used on both the drill bits and the bone pins.

The features corresponding to the standard half-drill have a letter "d" after the number, but otherwise the numbers correlate to the same features on the modified drill as they do on the standard half-drill in all the other figures. The modification includes a raised cutting edge 10 along one of the angled edges 4d'. The top of the cutting edge 10 as shown in FIG. 9 is level with the flat plane 2d. The cutting edge 10 has a relief angle 12, shown in FIG. 8b, of 25 to 35 degrees cut downward from the top of the raised edge 10 into the flat plane 2d and parallel to the angled edge. The relief angle 12 is preferably 30 degrees. The modified cutting edge also includes a clearance angle 13 of up to 8 degrees downward from the flat plane 2d and directed toward the raised angled edge 4d' and 10. The clearance angle 13 begins on the flat surface 2d at a distance spaced apart from the raised cutting edge to allow the clearance angle 13 to meet the relief angle 12 at a line below the level of the flat plane 2d, parallel to the raised edge 10 such that the raised edge 10 is approximately 0.3 to 0.5 millimeters in height. The preferred height of this edge is 0.38 millimeters. As in the standard half-drill bits and pins, the preferred angle $\alpha$ of the taper 3d is 45 degrees from the center axis of the cylindrical shaft 1d and $\alpha'$ is preferably 42 degrees from the center axis of the cylindrical shaft 1d. The preferred length of the cutting tip 9d is two to three centimeters.

This modified half-drill cutting tip offers all of the benefits that the standard half-drill does. It can be applied to the bone surface at an angle up to 40 degrees away from the perpendicular without slipping away from its initial location. A benefit of the modified half-drill over the standard half-drill is that with the modified version a surgeon is able to feel a light sensation when the drill penetrates through the wall of the cortical bone, and yet, as with the standard half-drill, the modified half-drill does not grab or lunge forward. It is an advantage to the surgeon to know when he has penetrated through the wall of the cortical bone, so he can know how far he has drilled.

As seen in Tables 1 and 2, the modified half-drill bone pin offers comparable temperature results to the standard half-drill bone pin. The modified embodiment also appears to have an average duration of temperature elevation above 55 degrees centigrade which is even less than the standard half-drill embodiment.

The method of drilling bone of this invention utilizes a half-drill in conjunction with bone drill bits and bone pins and has been described in the foregoing specification. A modified design of the half-drill has also been described. It will be understood that other modifications can be made without departing from the spirit and scope of the invention.

We claim:

1. In a method for inserting a bone pin through tissue and bone, the improvement comprising:
    drilling through said tissue and bone with a bone pin, said bone pin having an elongated cylindrical shaft with a cutting tip at one end of said shaft, said cutting tip including a semi-cylindrical portion having a flat surface substantially coinciding with the center plane of said bone pin, said semi-cylindrical portion having a proximal end integrally connected to the shaft and a distal end having an angled cutting edge and an angled non-cutting edge converging to form a point,
    maintaining the maximum average bone temperature during drilling at a radial distance of 1 mm from the drill site at about 51° C. or less, and maintaining the average duration of temperature elevation above 55° C. at a radial distance of 1 mm from the drill site during drilling at about one second or less; and
    retaining the bone pin in the tissue and bone for a period of time for use with a suitable external fixation device.

* * * * *